(12) United States Patent
Yamamoto et al.

(10) Patent No.: US 7,838,242 B2
(45) Date of Patent: Nov. 23, 2010

(54) NUCLEIC ACID LIGANDS CAPABLE OF BINDING TO INTERNALIN B OR INTERNALIN A

(75) Inventors: Cindy Yamamoto, Irvine, CA (US); Toshit Sen, Tustin, CA (US)

(73) Assignees: Hitachi Chemical Co., Ltd., Tokyo (JP); Hitachi Chemical Research Center, Irvine, CA (US)

( * ) Notice: Subject to any disclaimer, the term of this patent is extended or adjusted under 35 U.S.C. 154(b) by 0 days.

(21) Appl. No.: 12/374,480

(22) PCT Filed: Jul. 20, 2007

(86) PCT No.: PCT/US2007/074044
§ 371 (c)(1), (2), (4) Date: Jan. 20, 2009

(87) PCT Pub. No.: WO2008/011608
PCT Pub. Date: Jan. 24, 2008

(65) Prior Publication Data
US 2009/0264512 A1    Oct. 22, 2009

Related U.S. Application Data

(60) Provisional application No. 60/832,648, filed on Jul. 21, 2006, provisional application No. 60/876,929, filed on Dec. 22, 2006.

(51) Int. Cl.
*C12Q 1/68*    (2006.01)
(52) U.S. Cl. ................... 435/6; 435/91.1; 536/22.1; 536/23.1
(58) Field of Classification Search ................... None
See application file for complete search history.

(56) References Cited

U.S. PATENT DOCUMENTS

| | | |
|---|---|---|
| 5,270,163 A | 12/1993 | Gold et al. |
| 5,475,096 A | 12/1995 | Gold et al. |
| 5,756,291 A | 5/1998 | Griffin et al. |
| 5,792,613 A | 8/1998 | Schmidt et al. |
| 7,435,542 B2 | 10/2008 | Shi et al. |
| 7,645,582 B2 * | 1/2010 | Yamamoto et al. ............ 435/6 |
| 2002/0009811 A1 | 1/2002 | Bodenhamer et al. |
| 2004/0018530 A1 | 1/2004 | Bowser et al. |
| 2005/0003362 A1 | 1/2005 | Krylov et al. |
| 2005/0089893 A1 | 4/2005 | Lopez et al. |
| 2005/0282226 A1 | 12/2005 | Okada et al. |
| 2006/0008841 A1 | 1/2006 | Okada et al. |
| 2006/0078901 A1 | 4/2006 | Buchrieser et al. |
| 2006/0121489 A1 | 6/2006 | Gorenstein et al. |
| 2007/0207457 A1 | 9/2007 | Asai et al. |
| 2007/0243529 A1 | 10/2007 | Li et al. |
| 2008/0182759 A1 | 7/2008 | West et al. |
| 2008/0286788 A1 | 11/2008 | James et al. |
| 2009/0004644 A1 | 1/2009 | Kiel et al. |
| 2009/0029363 A1 | 1/2009 | Kage |

FOREIGN PATENT DOCUMENTS

| | | |
|---|---|---|
| WO | WO/2006/135527 | 12/2006 |
| WO | WO 2008/011608 | 1/2008 |

OTHER PUBLICATIONS

International Search Report for corresponding PCT application No. PCT/US07/74044, Oct. 1, 2008.
Ellington et al., In vitro selection of RNA molecules that bind specific ligands, Nature, 1990, vol. 346, pp. 818-822.
Gopinath et al., An RNA aptamer that distinguishes between closely related human influenza viruses and inhibits haemagglutanin-mediated membrane fusion, J Gen. Virol., 2006, vol. 87, pp. 479-487.
Tuerk et al., Systematic Evolution of Ligands by Exponential Enrichment: RNA Ligands to Bacteriophage T4 DNA Polymerase, Science, 1990, vol. 249, pp. 505-510.

* cited by examiner

*Primary Examiner*—Heather Calamita
(74) *Attorney, Agent, or Firm*—Knobbe, Martens, Olson & Bear LLP

(57) ABSTRACT

The present disclosure relates to the isolation of a novel reagent selected for its binding characteristics to the proteins internalin B or internalin A. InlB is a surface-localized protein of *Listeria monocytogenes* that binds and activates the receptor tyrosine kinase Met. InlB promotes invasion of a number of cells including hepatocytes, endothelial and epithelial cell lines and causes activation of the actin-mediated internalization of the bacterium. InlA belongs to a large group of surface-localized leucine-rich repeat (LRR) proteins identified in the *Listeria* genome. InlA enables *Listeria monocytogenes* to invade non-phagocytic cells such as those of the human intestinal epithelium and is sufficient for adhesion to and inducing uptake into epithelial cells. The disclosed nucleic acid ligands to internalin B and internalin A may be useful for determining the presence or absence of internalin B, internalin A, or *Listeria* in food, clinical or environmental samples; they may also be useful as an agent for combating *Listeria* infection by binding to and inactivating the infection-promoting inlB or inlA proteins. One object is to incorporate these nucleic acid ligands into an in vitro diagnostic or biosensor platform designed to detect the presence or absence of internalin B, internalin A, or *Listeria* in food, clinical or environmental samples. Another object is to employ these nucleic acid ligands in methods for treating or preventing *Listeria* infection.

11 Claims, 10 Drawing Sheets

| CLONE | SEQUENCE | BP | SEQ ID NO |
|---|---|---|---|
| 1.3, 5.3, 6.3 | CGGCAGGGCGGGGGGCT | 18 | 11 |
| 13.2 | CACGGGAGGGAAGGGTGGGCAAGTGGAGACACAAACTTTCA | 41 | 12 |
| 3.2 | CTGGGCTGGGAGGGTGGGCTATATATCTGTACATTTTTCGA | 41 | 13 |
| 18.2 | TTGGGTGGGAGGGACGGCTTGAGAACAAGAATCCGCAAATGTT | 41 | 14 |
| 19.2 | ATTGGGGGGGTGGGAGGGACGCAGCGCAATTTCCCAACGGT | 41 | 15 |
| 6.2 | CAAATGGGTTGGGAGGCCGGCAATAAAGCACTTACGTTGG | 41 | 16 |

*FIG. 1*

| SEQUENCE | BP | ID NO | SEQ ID NO |
| --- | --- | --- | --- |
| | | | |
| ATCCATGGGGCGGAGATGAGGGGGAGGAGGGCGGGTACCCGGTTGAT | 47 | A8 | 21 |
| ATCTAGGACTGGGTGGGAAGGGATGGGAAAAATGTCCGCGCCTCGAT | 47 | A9 | 22 |
| ATCAGCAACAAGTGTGGGTAAGGGGAGGGCGGGAATGGGATGATGAT | 47 | A4 | 23 |
| ATCGGATGTGGGCAGGGGGGGGTGGGAAACGATTACAGACACAAGAT | 47 | A6 | 24 |
| ATCGGGTTATAGTTAGCGGGTAGGGGAGGGAGGGTAGATAGCTCGAT | 47 | A10 | 25 |

*FIG. 7*

NUCLEIC ACID LIGANDS CAPABLE OF BINDING TO INTERNALIN B OR INTERNALIN A

BACKGROUND

1. Field

The present disclosure relates to novel nucleic acid ligands (aptamers) which bind to the targets internalin B (inlB) and internalin A (inlA) and other specific outer membrane proteins on *Listeria*. The described aptamer reagents can be used for screening samples such as food, clinical and environmental samples for the presence of internalin B, internalin A, and other specific proteins. The novel DNA aptamers can also potentially be used for various applications in which the presence or absence of *Listeria* is required.

2. Description of the Related Art

An estimated 76 million foodborne illnesses occur each year in the US with 325,000 hospitalizations and 5000 deaths (see Mead et al., "Food-Related Illness and Death in the United States," Emerg. Infect. Dis. 5, 607-625 (1999)). *Listeria monocytogenes* has been implicated in at least 11 human foodborne epidemics worldwide and is associated with foods that are ready-to-eat and can be consumed without cooking (see Ben Embarek, P. K., "Presence, Detection and Growth of *Listeria Monocytogenes* in Seafoods: a review," Int. J. Food Microbiol. 23, 17-34 (1994)). Although *Listeria monocytogenes* causes only 2500 cases of foodborne illness per year, it is responsible for 10% of the total foodborne-related deaths. The majority of human listeriosis cases occur in neonates, the elderly and immunocompromised individuals with case fatality rates of 20-40% (see Farber, et al., "*Listeria monocytogenes*, a Food-Borne Pathogen," Microbiol. Rev. 55, 476-511 (1991); Schuchat, et al. "Epidemiology of Human Listeriosis," Clin. Microbiol. Rev. 4, 169-183 (1991); "Update—Multistate Outbreak of Listeriosis," Centers for Disease Control & Prevention Morbid. Mortal. Weekly Rep. 47, 1117-1118 (1999); Jacquet, et al. "Investigations related to the epidemic strain involved in the French Listeriosis outbreak in 1992," Appl. Environ. Microbiol. 61, 2242-2246 (1995).) Because of the severity of the illness and association with foods that can be consumed without heating, the U.S. Food and Drug Administration (FDA) and Food Safety and Inspection Service (FSIS) established a zero tolerance policy for the presence of *Listeria monocytogenes* in ready-to-eat (RTE) foods in 1989.

The increasing governmental regulations and changing topography of food processing and manufacturing have spurred the development of faster, more sensitive and cost-effective technologies for pathogen detection. Currently, there are many different methods available for *Listeria monocytogenes* or *Listeria* spp. detection on the market. The most widely used methodology due to cost and sensitivity is the traditional microbiological method of plating. Although these methods are effective for recovery of *Listeria monocytogenes* from a variety of samples, the time to positive results is 5-7 days after sample collection. Rapid methods that use nucleic acid amplification and immunochemical techniques improve time-to-results compared to culture-based methods and offer possibilities of high throughput automation. The rapid methods currently on the market comprise of PCR, probe hybridization, enzyme-linked immunoassay (ELISA), enzyme-linked fluorescent assay (ELFA), lateral flow and magnetic bead-based methods. The time-to-results decreases to 2-4 days for these assays but most require enrichment steps to improve sensitivity and allow recovery of injured or stressed organisms.

The faster time-to-results and high throughput capabilities has created an increasing adoption of PCR methods into food testing, but the greater costs associated with their use compared with traditional culture methods and lack of universal acceptance, currently restricts the widespread use of molecular methods in general. PCR-based methods also have several limitations. Theoretically, PCR-based technology should provide the detection level of $\leq 1$ CFU/25 g food sample mandated by the zero tolerance regulation. Assay sensitivity, however, is complicated by a number of factors, including low contamination levels, large sample volumes relative to small reaction volumes, and inhibition of the PCR reaction by components of the food matrix and therefore, do not reach theoretical values (see Norton, D. M. (2002) J AOAC Int. 85, 505-515). Also, PCR only detects the presence of DNA and cannot indicate whether the pathogens are dead or alive.

In comparison, immunological methods rely on the interaction between specific antibodies to selectively capture, label or detect a target organism and is widely used and accepted for the detection and confirmation of specific microorganisms. The widespread use and acceptance of immunology-based methods has resulted in a vast array of commercial test kits for the detection of the common foodborne bacteria in foods including *Salmonella, Listeria, Campylobacter* and *E. coli* O157:H7. ELISAs, which are the most common format used for immunological detection, have detection limits of between $10^3$-$10^5$ cfu/mL (see Churchill, et al. "Detection of *Listeria monocytogenes* and the toxin listeriolysin O in food," J. Microbiol. Meth. 64, 141-170 (2006)). To achieve this detection limit often requires enrichment of the pathogens for at least 24 hours before the sample is adequate for detection by ELISA (see de Boer, et al. "Methodology for detection and typing of food borne microorganisms," Int. J. Food Microbiol. 50, 119-130 (1999)).

Despite the improved time-to-results of many rapid detection systems, the requirement of conventional cultural enrichment still remains an important limiting feature of these methods. Also, these methods lack the ability to detect biomolecules in real time. There is an increasing demand for simple, inexpensive and reliable tests to analyze food samples. Biosensor technology has the potential to meet these needs in real time or near real time (see Alocilja, et al., "Market analysis of biosensors for food safety," Biosensors and Bioelectronics 18, 841-846 (2003); Hall, "Biosensor technologies for detecting microbiological foodborne hazards," Microbes and Infection 4, 425-432 (2002); Deisingh, et al. "Biosensors for the detection of bacteria," Can. J. Microbiol. 50, 69-77 (2004)). Studies have shown that biosensors can detect a broad spectrum of analytes in complex samples with a minimum of sample pre-treatment (see Hall "Biosensor technologies for detecting microbiological foodborne hazards," Microbes and Infection 4, 425-432 (2002); Deisingh, et al. "Biosensors for the detection of bacteria," Can. J. Microbiol. 50, 69-77 (2004))

Biosensors for bacterial detection generally involve a biological recognition component such as receptors, nucleic acids or antibodies in contact with physical or chemical transducers. Depending on the method of signal transduction, biosensors can be divided into five basic types: electrochemical, optical, piezoelectric, thermal and magnetic. Recently, sensors have been developed for detection of *Listeria monocytogenes* (see Geng et al., "Detection of Low Levels of *Listeria monocytogenes* Cells by Using a Fiber-Optic Immunosensor," Applied and Environmental Microbiology 70, 6138-6146 (2004); Leonard, P., Hearty, S., Wyatt, G., Quinn, J., O'Kennedy, R. (2005) J. Food Prot. 68, 728-735; Leonard, et al., "A generic approach for the detection of whole *Listeria monocytogenes* cells in contaminated samples using surface plasmon resonance," Biosensors and Bioelectronics 19 1331-1335 (2004); Tims, T. B., Dickey, S. S., Demarco, D. R., Lim, D. V., "Detection of low levels of *Listeria monocytogenes* within 20 hours using an evanescent wave biosensor," (2001) Am. Clin. Lab. 20, 28-29). The sensitivity and specificity of these assays are dependent on the antibody that is used for detection. The sensitivity threshold for a fiber-optic immunosensor (Analyte 2000; Research International, Woodinville, Wash.) was measured to be approximately $10^3$ CFU/mL for a pure culture of *Listeria monocytogenes* and $10^4$ CFU/mL when grown with lactic acid bacteria (Geng et al., "Detection of Low Levels of *Listeria monocytogenes* Cells by Using a Fiber-Optic Immunosensor," Applied and Environmental Microbiology 70, 6138-6146 (2004)) The levels of detection compare with immunological methods as expected since antibodies were the capture agents in contact with the transducer. Both polyclonal and monoclonal antibodies have been used for biosensor studies. Polyclonal antibodies have been used as detection reagents for several decades (see Breitling, F., Dubel, S. (1999) Recombinant Antibodies. John Wiley and Sons Inc., New York, p. 154). Supplies are limited and repeated immunizations are required to replenish depleted stocks. Monoclonal antibodies, on the other hand, offer a continuous supply of homogeneous, well-characterized antibodies. The high cost, low yields and requirement of skilled labor are some of the problems associated with monoclonal antibody production.

Aptamers, first reported in 1990 (see Tuerk, C., Gold, L. (1990) Science 249, 505-510; Ellington et al., "In vitro selection of RNA molecules that bind specific ligands" Nature 346, 818-822 (1990)), offer themselves as ideal candidates for use as the biological recognition components in biosensors, possessing advantages over traditional antibodies for use in sensors (see Jayasena, "Aptamers: An Emerging Class of Molecules That Rival Antibodies in Diagnostics," Clin. Chem. 45:9, 1628-1650 (1999)). Aptamers are nucleic acid ligands that can be generated against amino acids, drugs, proteins and complex targets such as cells (see Gopinath, S. C., Misono, T. S., Kawasaki, K., Mizuno, T., Imai, M., Odagiri, T., Kumar, P. K., "An RNA aptamer that distinguishes between closely related human influenza viruses and inhibits hemagglutanin-mediated membrane fusion," (2006) J. Gen. Virol. 87, 479-487; Cerchia, L. et al., "Neutralizing Aptamers from Whole-Cell SELEX Inhibit the RET Receptor Tyrosine Kinase," PLoS Biol. 3, e123 (2005); Duconge, F., Pestourie, C., Boulay, J., Aissouni, Y., Gombert, K., Tavitian, B., de Franciscis, V., Libri, D. (2005) PLos Biol. 3, e123; Mori, T. et al., "RNA aptamers selected against the receptor activator of NF-kB acquire general affinity to proteins of the tumor necrosis factor receptor family," Nuc. Acids Res. 32, 6120-6128 (2004); Daniels, D. A. et al., "A tenascin-C aptamer identified by tumor cell SELEX: Systematic evolution of ligands by exponential enrichment," Proc. Natl. Acad. Sci. 100, 15416-15421 (2003). Numerous aptamers have been selected using this technique against a wide range of targets with selectivity, specificity and affinity equal and sometimes superior to those of antibodies. The technique in which these oligonucleotide ligands are obtained was termed SELEX (Systematic Evolution of Ligands by Exponential Enrichment) described in U.S. Pat. No. 5,475,096 and U.S. Pat. No. 5,270,163. The advantages of using aptamers over traditional antibodies for in vitro assays include: 1) ability to be denatured/renatured multiple times (reusable), 2) stable to long term storage and can be transported at ambient temperature, 3) adjusting selection conditions to obtain aptamers with properties desirable for in vitro assay, 4) produced by chemical synthesis resulting in little batch to batch variation, 5) selected through an in vitro process eliminating the use of animals, 6) ability to attach reporter molecules at precise locations (see O'Sullivan, C. K., "Aptasensors—the future of biosensing?," Anal. Bioanal. Chem. 372, 44-48 (2002)).

Aptamers have yet to be used in diagnostic or biosensor approaches for foodborne pathogen detection. The aptamers isolated against outer membrane proteins in *Listeria* may be used in diagnostic and biosensor detection technologies for food, clinical or environmental samples.

SUMMARY

An embodiment provides a method of assaying a sample for the presence of *Listeria monocytogenes*, comprising: exposing the sample to an aptamer that specifically binds a protein selected from the group consisting of *Listeria monocytogenes* internalin B protein and *Listeria monocytogenes* internalin A protein; and determining that *Listeria monocytogenes* is present in the sample when the aptamer binds the protein present in the sample.

In a further aspect, the aptamer comprises a nucleic acid molecule that comprises the sequence gggn$_z$gggh$_x$gggnggg (SEQ ID NOS: 1-5) wherein "n" indicates a, c, g, or t, "h" indicates a, c, or t, z is 1 or 2, and x is 1 or 2.

In a further aspect, the aptamer comprises a sequence selected from the group consisting of SEQ ID NOS:1 and 2.

In a further aspect, the aptamer comprises a sequence selected from the group consisting of SEQ ID NOS:13 and 16.

In a further aspect, the aptamer comprises a sequence selected from the group consisting of SEQ ID NOS:3 and 4.

In a further aspect, the aptamer comprises a sequence selected from the group consisting of SEQ ID NOS:11, 14, and 15.

In a further aspect, the aptamer comprises the sequence of SEQ ID NO:5.

In a further aspect, the aptamer comprises the sequence of SEQ ID NO: 12.

In a further aspect, the aptamer comprises a nucleic acid sequence selected from the group consisting of SEQ ID NOS: 21, 22, and 23.

In a further aspect, the aptamer comprises a nucleic acid molecule that comprises the sequence gggyaggggrgggwggg (SEQ ID NO:18) wherein "y" indicates c or t; "r" indicates g or a; and "w" indicates t or a.

In a further aspect, the aptamer comprises a nucleic acid sequence selected from the group consisting of SEQ ID NOS: 24 and 25.

In an embodiment, a method of treating *Listeria monocytogenes* infection in a mammal is provided, comprising administering to the mammal an aptamer that specifically binds a protein selected from the group consisting of *Listeria monocytogenes* internalin B protein and *Listeria monocytogenes* internalin A protein at a concentration sufficient to reduce *Listeria monocytogenes* infection.

In a further aspect, the aptamer comprises a nucleic acid molecule that comprises the sequence gggn$_z$gggh$_x$gggnggg (SEQ ID NOS:1-5) wherein "n" indicates a, c, g, or t, "h" indicates a, c, or t, z is 1 or 2, and x is 1 or 2.

In a further aspect, the aptamer comprises a sequence selected from the group consisting of SEQ ID NOS:1 and 2.

In a further aspect, the aptamer comprises a sequence selected from the group consisting of SEQ ID NOS:13 and 16.

In a further aspect, the aptamer comprises a sequence selected from the group consisting of SEQ ID NOS:3 and 4.

In a further aspect, the aptamer comprises a sequence selected from the group consisting of SEQ ID NOS:11, 14, and 15.

In a further aspect, the aptamer comprises the sequence of SEQ ID NO:5.

In a further aspect, the aptamer comprises the sequence of SEQ ID NO:12.

In a further aspect, the aptamer comprises a nucleic acid sequence selected from the group consisting of SEQ ID NOS: 21, 22, and 23.

In a further aspect, the aptamer comprises a nucleic acid molecule that comprises the sequence gggyaggggrgggwggg (SEQ ID NO:18) wherein "y" indicates c or t; "r" indicates g or a; and "w" indicates t or a.

In a further aspect, the aptamer comprises a nucleic acid sequence selected from the group consisting of SEQ ID NOS: 24 and 25.

In an embodiment, an aptamer is provided that comprises a nucleic acid molecule that comprises the sequence $gggn^1_zgggh_xggg n^2ggg$ (SEQ ID NOS:1-5), wherein $n^1$ is a, z is 1, h is c, x is 1, and $n^2$ is g.

In a further aspect, the aptamer comprises the sequence of SEQ ID NO:11.

In an embodiment, an aptamer is provided that comprises a nucleic acid molecule that comprises the sequence $gggn^1_zgggh_xgggn^2ggg$ (SEQ ID NOS:1-5), wherein n is a, z is 1, h is a, x is 2, and $n^2$ is t.

In a further aspect, the aptamer comprises the sequence of SEQ ID NO:12.

In an embodiment, an aptamer is provided that comprises a nucleic acid molecule that comprises the sequence $gggn^1_zgggh_xgggn^2ggg$ (SEQ ID NOS:1-5), wherein $n^1$ is c or t, z is 2, h is a, x is 1, and $n^2$ is t.

In a further aspect, the aptamer comprises the sequence of SEQ ID NO:13.

In an embodiment, an aptamer is provided that comprises a nucleic acid molecule that comprises the sequence $gggn^1_zgggh_xgggn^2ggg$ (SEQ ID NOS:1-5), wherein $n^1$ is t, z is 1, h is a, x is 1, and $n^2$ is a.

In a further aspect, the aptamer comprises the sequence of SEQ ID NO:14.

In an embodiment, an aptamer is provided that comprises a nucleic acid molecule that comprises the sequence $gggn^1_zgggh_xgggn^2ggg$ (SEQ ID NOS:1-5), wherein $n^1$ is g, z is 1, h is t, x is 1, and $n^2$ is a.

In a further aspect, the aptamer comprises the sequence of SEQ ID NO:15.

In an embodiment, an aptamer is provided that comprises a nucleic acid molecule that comprises the sequence $gggn^1_zgggh_xgggn^2ggg$ (SEQ ID NOS:1-5), wherein $n^1$ is t, z is 2, h is a, x is 1, and $n^2$ is c.

In a further aspect, the aptamer comprises the sequence of SEQ ID NO:16.

In an embodiment, an aptamer is provided that comprises a nucleic acid molecule that comprises a sequence selected from the group consisting of SEQ ID NOS:21, 22, and 23.

In an embodiment, an aptamer is provided that comprises a nucleic acid molecule that comprises a sequence gggyaggggrgggwggg (SEQ ID NO:18) wherein "y" indicates c or t; "r" indicates g or a; and "w" indicates t or a.

In a further aspect, the aptamer comprises a nucleic acid sequence selected from the group consisting of SEQ ID NOS: 24 and 25.

BRIEF DESCRIPTION OF THE DRAWINGS

FIG. 1 is a list of DNA sequences obtained after round 15 of an in vitro selection procedure (29, U.S. Patent App. No. 20050142582) to obtain high affinity aptamers against internalin B. The four repeats of three Gs in each sequence are highlighted.

FIG. 7 shows aptamer sequences (SEQ ID NOS:21-25) that bound to internalin A based on strong signals in the ELISA screen compared to binding with the aptamer library.

DETAILED DESCRIPTION OF THE PREFERRED EMBODIMENTS

Figure 2:
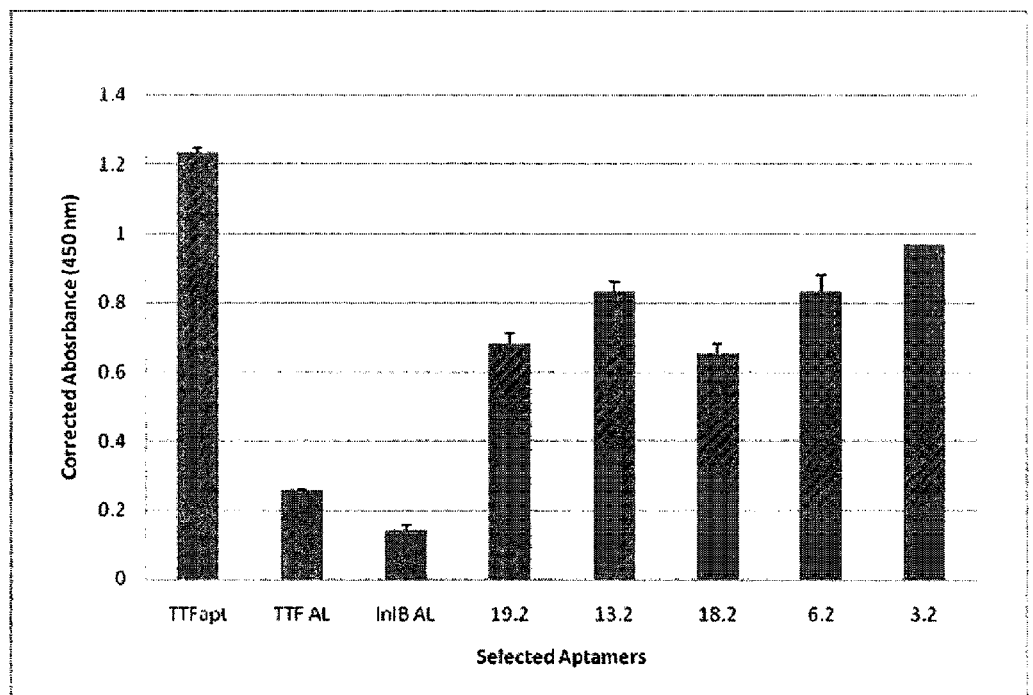
FIG. 2 is a chart showing the results of an ELISA used to screen for selected oligonucleotides that bound to histidine-tagged internalin B attached to a microplate. A previously identified aptamer (TTFapt) against the transcription factor, TTF, was used as a control (29, U.S. Patent App. No. 20050142582). The initial oligonucleotide library (TTF AL, inlB AL) was used as a negative control with histidine-tagged TTF and histidine-tagged inlB protein bound to the microplate. The data represents the average±S.D. of n=3.

The present disclosure relates to the isolation of novel reagents selected for their binding characteristics to the proteins internalin B and internalin A. InlB is a surface-localized protein of *Listeria monocytogenes* that binds and activates the receptor tyrosine kinase Met (see Shen, Y et al., "InlB-Dependant Internalization of *Listeria* Is Mediated by the Met Receptor Tyrosine Kinase," Cell 103, 501-510 (2000)). InlB promotes invasion of a number of cells including hepatocytes, endothelial and epithelial cell lines (see Bierne, H. et al., "InlB, a surface protein of *Listeria monocytogenes* that behaves as an invasion and a growth factor," J. Cell Sci. 115, 3357-3367 (2002); Cabanes, D. et al., "Surface proteins and the pathogenic potential of *Listeria monocytogenes*," Trends Microbiol. 10, 238-245 (2002)) and causes activation of the actin-mediated internalization of the bacterium. InlA belongs to a large group of surface-localized leucine-rich repeat (LRR) proteins identified in the *Listeria* genome. InlA enables *Listeria monocytogenes* to invade non-phagocytic cells such as those of the human intestinal epithelium (see Gaillard, J. L., Berche, P., Frehel, C., Gouin, E., Cossart, P., "Entry of *L. monocytogenes* into Cells Is Mediated by Internalin, a Repeat Protein Reminiscent of Surface Antigens from Gram-Positive Cocci," (1991) Cell 65, 1127-1141) and is sufficient for adhesion to and inducing uptake into epithelial cells (see Schubert W. D., Urbanke, C., Ziehm, T., Beier, V., Machner, M. P., Domann, E., Wehland, J., Chakraborty, T., Heinz, D. W., "Structure of Internalin, a Major Invasion Protein of *Listeria monocytogenes*, in Complex with Its Human Receptor E-Cadherin," (2002) Cell 111, 825-836).

The disclosed nucleic acid ligands to internalin B and internalin A may be useful for determining the presence or absence of internalin B, internalin A, or *Listeria* in food, clinical or environmental samples; they may also be useful as an agent for combating *Listeria* infection by binding to and inactivating the infection-promoting inlB and inlA proteins. One object is to incorporate these nucleic acid ligands into an in vitro diagnostic or biosensor platform designed to detect the presence or absence of internalin B, internalin A, or *Listeria* in food, clinical or environmental samples. Another object is to employ these nucleic acid ligands in methods for treating or preventing *Listeria* infection.

Disclosed are oligonucleotides that bind the internalin B and internalin A proteins. Specific oligonucleotide sequences of aptamers specific to internalin B are shown in FIG. 1 as SEQ ID NOS:11-16. Furthermore, specific oligonucleotide sequences of aptamers specific to internalin A are shown in Table 1 as SEQ ID NOS:21-25. These oligonucleotides could be useful as biological recognition elements in biosensor platforms and/or in vitro diagnostic assays, or as therapeutic agents for listeriosis cases. The oligonucleotides relevant to internalin B comprise 18-41 nucleotides, while those relevant to internalin A comprise 47 nucleotides. The oligomers are composed of nucleotides, modified nucleotides or a combination thereof. Modified nucleotides can include, but are not limited to, the addition of biotin, thio, iodo, bromo, phosphor, fluoro or amino groups. Preferably, the oligonucleotides are composed of DNA but can also be RNA or synthetic nucleotide analogs. If the oligonucleotides are to be used in biosensor applications, 5', 3' or internal modifications to the nucleotides can be used to bind the oligonucleotide to the biosensor platform that may be electrochemical, optical, piezoelectric, magnetic or calorimetric.

I. Aptamers to Internalin B

Each of the isolated sequences of aptamers to internalin B contains a G-rich sequence in the form of four repeats of three dGTPs highlighted in FIG. 1. The G-rich sequence appears to be essential in the binding to internalin B protein based on truncation studies of aptamer 3.2 using ELISA. Based on binding affinities, several G-rich sequences that provide a high level of binding affinity to inlB have been deduced and are disclosed below.

| | |
|---|---|
| $gggn_zgggn_xgggnggg$ | |
| $gggn_zgggh_xgggnggg$ | |
| $gggdgggh_xgggdggg$ | |
| gggyygggrgggyggg | (SEQ ID NO: 1) |
| gggytgggagggyggg | (SEQ ID NO: 2) |
| gggngggh gggrggg | (SEQ ID NO: 3) |
| gggdggghgggrggg | (SEQ ID NO: 4) |
| gggrgggrrgggyggg | (SEQ ID NO: 5) |

In these sequences, "n" indicates a, c, g, or t; "y" indicates c or t; "d" indicates g, t, or a; "h" indicates a, c, or t; and x and z are 1 or 2.

A. Isolation and Characterization of Aptamer Reagents

The following describe the methods used to isolate and characterize the described internalin B aptamer reagents.

1. Preparation of the Recombinant Internalin B

Primers for inlB were designed using *Listeria monocytogenes* sequence from GenBank Accession Number AJ012346. The 5' ends of the primer sequence include LIC sequences for simplified cloning in later steps. The sequences of the PCR primers are as follows: inlB-S, 5'-GGT ATT GAG GGT CGC GCG AAA GTA CAA GCG-3' (SEQ ID NO:6), inlB-AS, 5'-AGA GGA GAG TTA GAG CCT TTC TGT GCC CTT AAA T-3' (SEQ ID NO:7). InlB was amplified by PCR from *Listeria monocytogenes* genomic DNA (ATCC, 19115D). The PCR product was treated for LIC cloning and inserted in-frame upstream from the His-tag sequence in the pET-30 Xa/LIC vector (Novagen). The nucleotide sequence of the amplified inlB fragment was verified by sequencing. For expression of the recombinant protein, the resulting plasmid pET30/inlB was transformed into *Escherichia coli* strain BLR(DE3).

2. Purification of Recombinant Internalin B

*E. coli* BLR(DE3) transformed with pET30/inlB was grown at 37° C. until an OD600 of 0.7 and then induced with 1 mM IPTG for 3 hours. The induced bacteria were harvested by centrifugation and the pellet was kept at −80° C. overnight. The pellet was resuspended in column binding buffer (50 mM HEPES, pH 7.9, 5 mM imidazole, 500 mM NaCl) and protease inhibitors before sonication on ice. Debris was removed by centrifugation and protein was purified by metal affinity chromatography (Novagen). Protein concentration was determined by BCA assay and purity was analyzed using SDS-PAGE and western blot.

3. In Vitro Selection of Aptamers

The methods followed are described in detail in Murphy, M. D., Fuller, S. T., Richardson, P. M. & Doyle, S. A., "An improved method for the in vitro evolution of aptamers and applications in protein detection and purification," (2003) Nuc. Acids Res. 31, No. 18 e100, and in United States Patent Application, Publication No. 2005/0142582, which is incorporated here by reference. In brief, this method involves (a) preparing a target molecule with a polyhistidine affinity tag for magnetic beads; (b) binding the target molecule to magnetic beads and contacting the target molecule with a library of aptamer sequences to allow binding of aptamer sequences to the target molecule thus forming bead-target-aptamer sequence complexes, wherein the aptamer sequences are comprised of degenerate sequences; (c) separating bead-target-aptamer sequence complexes from non-binding aptamer sequences by retaining the target molecule on its bead and removing unbound aptamer sequences; then (d) separating target-bound aptamer sequences from said magnetic beads to form a pool of binding aptamer sequences; (e) amplifying the binding aptamer sequences; and (f) iteratively repeating steps (b) through (d) a sufficient number of times to result in identification of at least one aptamer sequence having high affinity for the target molecule.

SELEX protocols to isolate aptamers against inlB were obtained from Dr. Sharon Doyle (see Murphy, M. B., Fuller, S. T., Richardson, P. M. & Doyle, S. A., "An improved method for the in vitro evolution of aptamers and applications in protein detection and purification," (2003) Nuc. Acids Res. 31, No. 18 e110; U.S. Patent App. Publication No. 2005/0142582) with some modifications as described below. Protein-bound Ni-NTA magnetic beads were prepared by equilibrating 150 µL of Ni-NTA magnetic beads (Qiagen, Valencia, Calif.) into PBS-T (50 mM $K_2HPO_4$, pH 7.5, 150 mM NaCl, 0.05% Tween-20). The equilibrated beads were resuspended in 800 µL PBS-T and 16 µL 3.2 mg/mL purified internalin B was added and mixed with rotation for 30 min at 4° C. The bead-bound internalin B was then washed 3× with 1 mL PBS-T, and diluted to 5 pmol/µL with PBS-T and stored at 4° C.

For initial selection, 1 nmol aptamer library (5'-GGTAT-TGAGGGTCGCATC-40N-GATGGCTCTAACTCTC-CTCT, SEQ ID NO:8) was heated to 95° C. for 2 min then immediately cooled to 4° C. and hybridized with 100 pmol magnetic bead (Ni-NTA magnetic beads, Qiagen) bound inlB protein for 30 min at 37° C. in a volume of 10 mL PBS-T containing 1 µg/mL BSA, 0.1 µg/mL dIdC. InlB-coated nickel magnetic beads were prepared fresh for each round of selection and was required to maintain selection. From round 2, the hybridizations of isolated oligos and inlB-coated magnetic beads were only 15 min at 37° C. The amount of protein decreased from 100 pmol at round 2 to 20 pmol by round 12. A Dynal magnetic stand was used to isolate the oligos bound to the inlB protein from the unbound. The beads were washed 3 times in 1 mL PBS-T (50 mM $K_2HPO_4$, pH 7.5, 150 mM NaCl, 0.05% Tween-20) and resuspended in 10 µL 20 mM Tris pH 7.5, 500 mM imidazole. The entire sample was added to a 100 µL volume PCR reaction which included LIC-F (5'-ggtattgagggtcgcatc-3', SEQ ID NO:9) and biotinylated LIC-R (5'-agaggagagttagagccatc-3', SEQ ID NO:10) primers. Amplification conditions were 2 min at 95° C.; 11-15 cycles of 30 s at 95° C., 30 s at 58° C., 30 s at 68° C.; and 2 min at 68° C. Following PCR, 10 µL was analyzed on a 1.2% agarose gel stained with ethidium bromide while the remaining 90 µL was used for the isolation of the non-biotinylated aptamer strand. 90 µL of the PCR product and 23 µL 5M NaCl were then mixed with 1 mg of M-280 streptavidin magnetic beads (Invitrogen, Carlsbad, Calif.) for 10 min at room temperature, then washed 3×1 mL with PBS-T. Single-stranded aptamers were separated from the immobilized complementary strand using a 5 min incubation of 50 µL of fresh 100 mM NaOH. The tubes were applied to a magnet and the ssDNA was removed and diluted into 1 mL PBS-T, containing 10 µL of 100 mM monobasic phosphate buffer to adjust the pH to 7.5. Finally, the material was heated to 95° C. for 2 min then immediately placed at 4° C. until the next round of selection.

In order to remove aptamers that bind to the Ni-NTA magnetic beads, counter-selection was performed after rounds 3, 6, 9 and 12. A 20 µL aliquot of a 5% slurry of Ni-NTA-magnetic beads was added to the 1 mL of ssDNA in PBS-T and incubated for 10 min with rotation, then applied to a magnet and the supernatant removed for the next round. Amplified PCR products were cloned after round 15 into pET30/Xa vector and sequenced. Sequences were aligned using ClustalW (Higgins, D., Thompson, J., Gibson, T., "CLUSTAL W: improving the sensitivity of progressive multiple sequence alignment through sequence weighting, position-specific gap penalties and weight matrix choice," (1994) Nuc. Acids Res. 22, 4673-4680). The sequences of several aptamers resulting from this process are shown in FIG. 1 as SEQ ID NOS:11-16. In the Figure, the four repeats of three Gs in each sequence that are apparently involved in binding to internalin B are highlighted.

4. ELISA Screening of Aptamers

Figure 3:
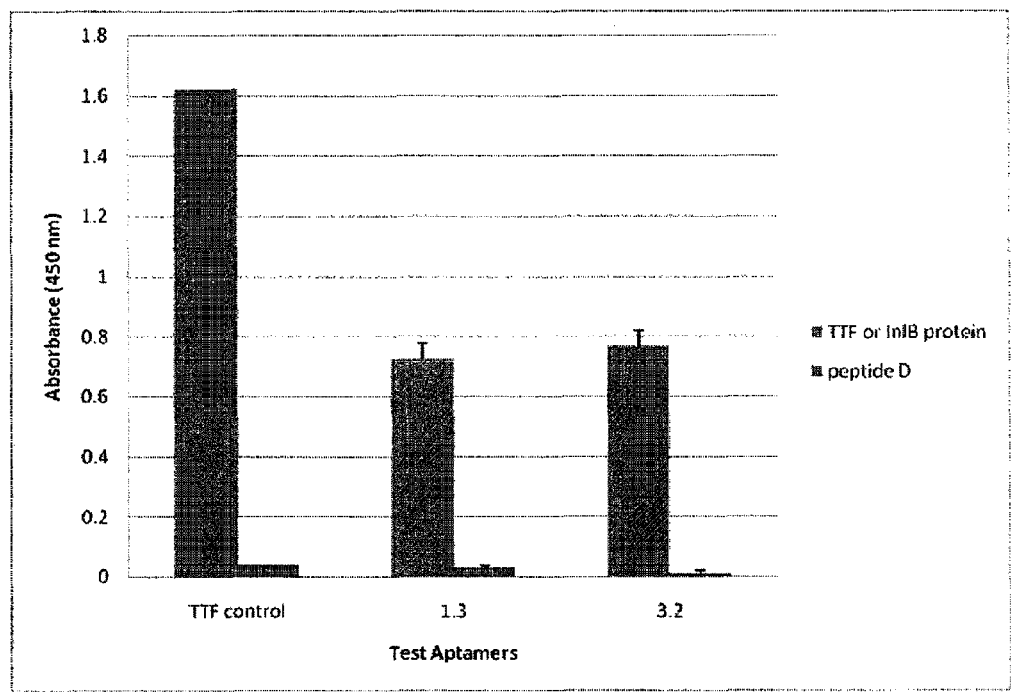
FIG. 3 is a chart showing the results of an ELISA used to test specificity of selected aptamers. Histidine-tagged TTF, inlB or peptide D (amino acid sequence: QQQTAPKAPTE-HHHHHH, SEQ ID NO:17) was attached to the microplate. The amount of selected aptamer bound to inlB or peptide D was determined by absorbance measured. The data represents the average±S.D. of n=3.

A nickel-coated microplate (HisSorb, Qiagen) was used to bind 500 ng his-tagged TTF1, peptide D or inlB to the plate as per manufacturer's directions. Biotinylated aptamers (5 ng/µmL) were heated to 95° C. for 3 minutes and quickly cooled to 4° C. for 5 minutes before application to each well. The biotinylated aptamers were incubated with the bound proteins in the HisSorb plate overnight at 4° C. with gentle shaking. Wells were then washed four times with 200 µL PBS-T. Streptavidin-horseradish peroxidase was added to the wells for 30 minutes at room temperature with gentle shaking. The wells were washed as described previously before development with TMB (Pierce). The reactions were stopped with 1M $H_2SO_4$ and absorbance was measured at 450 nm using a ThermoMax microplate reader (Molecular Devices). The results are shown in FIG. 2. In FIG. 2, a previously identified aptamer (TTFapt) against the transcription factor, TTF, was used as a control (see Murphy, M. B., Fuller, S. T., Richardson, P. M. & Doyle, S. A., "An improved method for the in vitro evolution of aptamers and applications in protein detection and purification," (2003) Nuc. Acids Res. 31, No. 18 e110, U.S. Patent App. No. 2005/0142582). The initial oligonucleotide library (TTF AL, inlB AL) was used as a negative control with histidine-tagged TTF and histidine-tagged inlB protein bound to the microplate. The data represents the average±S.D. of n=3. Furthermore, FIG. 3 shows the results of an ELISA used to test the specificity of selected aptamers. Histidine-tagged TTF, inlB or peptide D (amino acid sequence: QQQTAPKAPTEHHHHHH (SEQ ID NO: 17)) was attached to the microplate. The amount of selected aptamer bound to inlB or peptide D was determined by absorbance measured. The data represents the average±S.D. of n=3.

5. Competitive ELISA

Figure 4:
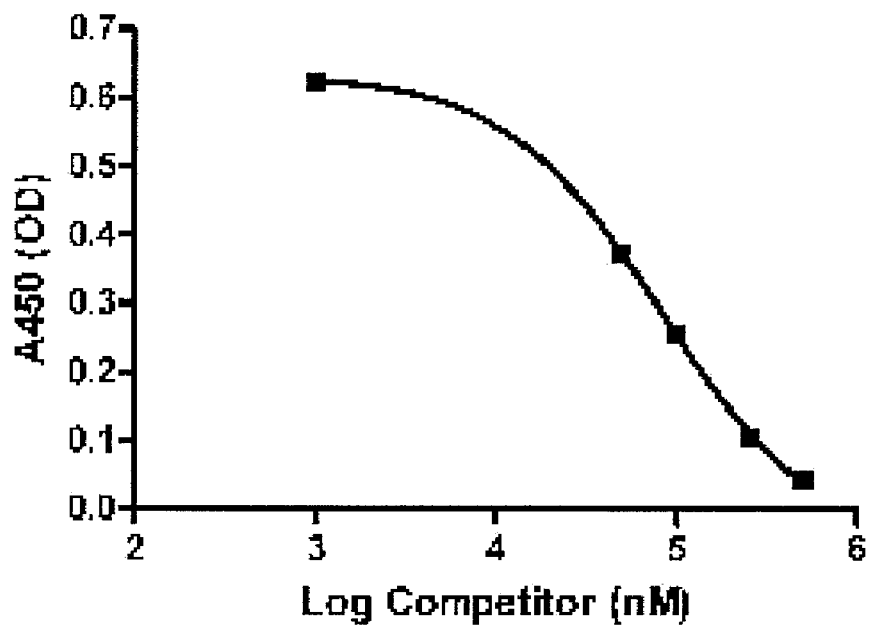
FIG. 4 is data obtained using a competitive ELISA for internalin B aptamer clone 3.2. The data was input into a sigmoidal model equation, a+(b−a)/(1+10^(x−c)), to obtain an EC50=82.7 µM.

The competitive ELISA was used to measure EC50 (50% effective concentration). A specified amount of internalin B (500 ng) was coated on the plate. 5 ng/uL biotinylated aptamer 3.2 was incubated with increasing amounts of non-biotinylated aptamer 3.2 and then applied to the coated plates. The amount of internalin B and biotinylated aptamer 3.2 to use in these experiments was determined from the linear range of dose response curves. Using GraphPad Prism 4 software, the Sigmoidal model (equation: $a+(b-a)/(1+10^{\wedge}(x-c))$) was used to determine EC50. The best-fit value of EC50 was determined to be 82 uM. The results are shown in FIG. 4.

6. Western Blot Analysis

Figure 5:
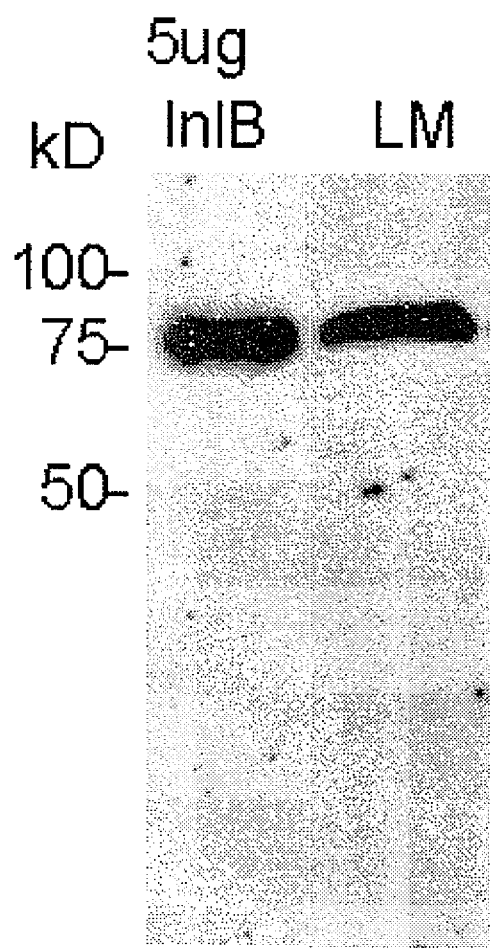
FIG. 5 is a western blot analysis of 5 µg purified inlB and 10 mL Listeria monocytogenes extract run on a 10% SDS-PAGE gel and probed with biotinylated internalin B aptamer clone 3.2. The aptamer was detected with streptavidin-labeled HRP and chemiluminescent substrate.

Purified recombinant inlB and a *Listeria monocytogenes* protein extract was loaded onto a 10% SDS-PAGE gel. A single *Listeria monocytogenes* colony was inoculated into 10 mL BHI (Brain Heart Infusion) media and grown overnight at 37° C. Cells were pelleted and harvested with 50 µL Laemmli Buffer. The gel was loaded with 5 µg purified recombinant his-tagged inlB and 25 µL *Listeria monocytogenes* extract and run at 160V for 1 hour. Proteins were transferred to 0.45 µm nitrocellulose at 100V for 1 hour. Protein transfer was checked using Ponceau S followed by blocking with 5% NFDM (non-fat dried milk). The blot was incubated with 5 ng/uL biotinylated aptamer 3.2 for 1 hour in 5% NFDM. The bound biotinylated aptamer was detected with streptavidin-HRP and Supersignal West Pico Chemiluminescent substrate (Pierce). The results are shown in FIG. 5.

II. Aptamers to Internalin A

Also disclosed are oligonucleotides that bind internalin A protein. These oligonucleotides could be useful as biological recognition elements in biosensor platforms and/or in vitro diagnostic assays. The oligonucleotides disclosed comprise 47 nucleotides. The oligomers are composed of nucleotides, modified nucleotides or a combination thereof. Modified nucleotides can include, but are not limited to, the addition of biotin, thio, iodo, bromo, phosphor, fluoro or amino groups. Preferably, the oligonucleotides are composed of DNA but can also be RNA or synthetic nucleotide analogs. If the oligonucleotides are to be used in biosensor applications, 5', 3' or internal modifications to the nucleotides can be used to bind the oligonucleotide to the biosensor platform that may be electrochemical, optical, piezoelectric, magnetic or calorimetric.

Each of the isolated sequences contains a G-rich sequence in the form of four repeats of three dGTPs. Based on binding affinities, one consensus G-rich sequence that provides a high level of binding affinity to inlA has been deduced and is disclosed below.

gggyaggggrgggwggg (SEQ ID NO:18)

In this sequence, "y" indicates c or t; "r" indicates g or a; and "w" indicates t or a.

A. Isolation and Characterization of Aptamer Reagents

The following describe the methods used to isolate and characterize the described aptamer reagents.

1. Preparation of the Recombinant Internalin A

Bacterial DNA coding for *Listeria monocytogenes* protein internalin A: residues 30-766 was PCR amplified from genomic DNA (ATCC #19115D). The primers were designed with Web Primer (http://genome-www2.stanford.edu/cgi-bin/SGD/web-primer) using the sequence from Genbank Accession Number CAC98512. The primers had the following sequences inlA-S, 5'-GGT ATT GAG GGT CGC ACA AAT GCT CAG GCA GCT-3' (SEQ ID NO:19); inlA-AS, 5'-AGA GGA GAG TTA GAG CCT TA TGA AGC TTC TTT TGA ATT-3' (SEQ ID NO:20). The 5' (underlined) region of the primers includes sequences required for a Ligation Independent Cloning (LIC) strategy. The PCR product was treated for LIC cloning and inserted in-frame upstream from the His-tag sequence in the pET-30 Xa/LIC vector (Novagen). The nucleotide sequence of the amplified inlA fragment was verified by sequencing. For expression of the recombinant protein, the resulting plasmid pET30/inlA was transformed into *Escherichia coli* strain BL21(DE3)plysS.

2. Purification of Recombinant Internalin A

*E. coli* BL21(DE3)plysS transformed with pET30/inlA was grown at 37° C. until an OD600 of 0.7 and then induced with 1 mM IPTG for 3 hours. The induced bacteria were harvested by centrifugation and the pellet was kept at −20° C. overnight. The pellet was resuspended in 5.0 mL of Bugbuster Protein Extraction Reagent (EMD Biosciences) containing 30,000 U rlysozyme (recombinant lysozyme; EMD Biosciences), 125 U Benzonase nuclease (EMD Biosciences) and 50 μL Sigma P1 protease inhibitor. The cell suspension was incubated at room temperature for 10 min. Cell debris was removed by centrifugation and the protein was purified by metal affinity chromatography using Ni Sepharose 6 fast flow. A buffer consisting of 50 mM sodium phosphate buffer pH 8.0, 500 mM sodium chloride, and 50 μL Sigma P1 protease inhibitor was used for column washing and the bound protein was eluted with 5 mL of 50 mM sodium phosphate buffer pH 8.0, 500 mM sodium chloride, and 50 μL Sigma P1 protease inhibitor. Protein concentration was determined by the Bio-Rad protein assay (Bradford method) and purity was analyzed using SDS-PAGE.

3. Aptamer Selection against Recombinant Internalin A

The methods followed are described in detail in Murphy, M. B., Fuller, S. T., Richardson, P. M. & Doyle, S. A., "An improved method for the in vitro evolution of aptamers and applications in protein detection and purification," (2003) Nuc. Acids Res. 31, No. 18 e110), and in United States Patent Application, Publication No. 2005/0142582, which is incorporated here by reference. In brief, this method involves (a) preparing a target molecule with a polyhistidine affinity tag for magnetic beads; (b) binding the target molecule to magnetic beads and contacting the target molecule with a library of aptamer sequences to allow binding of aptamer sequences to the target molecule thus forming bead-target-aptamer sequence complexes, wherein the aptamer sequences are comprised of degenerate sequences; (c) separating bead-target-aptamer sequence complexes from non-binding aptamer sequences by retaining the target molecule on its bead and removing unbound aptamer sequences; then (d) separating target-bound aptamer sequences from said magnetic beads to form a pool of binding aptamer sequences; (e) amplifying the binding aptamer sequences; and (f) iteratively repeating steps (b) through (d) a sufficient number of times to result in identification of at least one aptamer sequence having high affinity for the target molecule.

The aptamers were selected by the SELEX procedure described by Dr. Sharon Doyle (see Murphy, M. B., Fuller, S. T., Richardson, P. M. & Doyle, S. A., "An improved method for the in vitro evolution of aptamers and applications in protein detection and purification," (2003) Nuc. Acids Res. 31, No. 18 e110, see also U.S. Patent App. Publication No. 2005/0142582) used with some modifications, as described below. Protein-bound Ni-NTA magnetic beads were prepared by equilibrating 150 μL of Ni-NTA magnetic beads (Qiagen, Valencia, Calif.) into PBS-T (50 mM K2HPO4, pH 7.5, 150 mM NaCl, 0.05% Tween-20). The equilibrated beads were resuspended in 1250 μL PBS-T and 25 μL 2 mg/mL purified internalin A was added and mixed with rotation for 30 min at 4° C. The bead-bound internalin A was then washed 3× with 1 mL PBS-T, and diluted to 5 pmol/μL with PBS-T and stored at 4° C.

For initial selection, 1 nmol aptamer library (5'-GGTATTGAGGGTCGCATC-40N-GATGGCTCTAACTCTCCTCT, SEQ ID NO:8) was heated to 95° C. for 2 min then immediately cooled to 4° C. and hybridized with 100 pmol magnetic bead (Ni-NTA magnetic beads, Qiagen) bound inlA protein for 30 min at 37° C. in a volume of 10 mL PBS-T containing 1 μg/mL BSA, 0.1 μg/mL dIdC. InlA-coated nickel magnetic beads were prepared fresh for each day and used for 2 rounds of selection. A Dynal magnetic stand was used to isolate the oligos bound to the inlA protein from the unbound. The beads were washed 3 times in 1 mL PBS-T and resuspended in 10 μL 20 mM Tris pH 7.5, 500 mM imidazole.

To increase the stringency of binding/wash conditions, the amount of protein and incubation time was decreased whereas numbers of washes were increased along the process as shown in Table 1. Counter selection using 20 μL of Ni-NTA magnetic agarose beads was performed after rounds 4 and 9.

TABLE 1

| Round | Protein amount (pmol) | dIdC (ug/ml) | Incubation Time (min) | Wash |
|---|---|---|---|---|
| 1 | 200 | 0 | 30 | 2× |
| 2 | 200 | 0 | 30 | 2× |
| 3 | 100 | 0 | 30 | 2× |
| 4 | 100 | 0 | 30 | 3× |
| 5 | 50 | 0 | 30 | 3× |
| 6 | 50 | 0.1 | 25 | 3× |
| 7 | 50 | 1 | 25 | 3× |
| 8 | 50 | 1 | 25 | 3× |
| 9 | 50 | 1 | 20 | 3× |
| 10 | 25 | 1 | 20 | 3× |
| 11 | 25 | 1 | 15 | 3× |
| 12 | 25 | 1 | 15 | 4× |
| 13 | 25 | 1 | 10 | 4× |
| 14 | 25 | 1 | 10 | 4× |

After beads were resuspended in 10 μL 20 mM Tris pH 7.5, 500 mM imidazole, the sample was added to a 100 μL volume PCR reaction which included LIC-F (5'-ggtattgagggtcgcatc-3', SEQ ID NO:9) and biotinylated LIC-R (5'-agaggagagtta-gagccatc-3', SEQ ID NO:10) primers. Amplification conditions were 2 min at 95° C.; 12-15 cycles of 30 s at 95° C., 30 s at 58° C., 30 s at 68° C.; and 2 min at 68° C. Following PCR, 5 μL was analyzed on a 1.2% agarose gel stained with ethidium bromide while the remaining 90 μL was used for the isolation of the non-biotinylated aptamer strand. 90 μL of the PCR product and 23 μL 5M NaCl were then mixed with 1 mg of M-280 streptavidin magnetic beads (Invitrogen, Carlsbad, Calif.) for 10 min at room temperature, then washed 3×1 mL with PBS-T. Single-stranded aptamers were separated from the immobilized complementary strand using a 5 min incubation of 50 μL of fresh 100 mM NaOH. The tubes were applied to a magnet and the ssDNA was removed and diluted into 1 mL PBS-T, containing 10 μL of 100 mM monobasic phosphate buffer to adjust the pH to 7.5. Finally, the material was heated to 95° C. for 2 min then immediately placed at 4° C. until the next round of selection. Amplified PCR products were cloned after round 15 into pET30/Xa vector and sequenced. Sequences were aligned using Geneious (Drummond A J, Kearse M, Heled J, Moir R, Thierer T, Ashton B, Wilson A, Stones-Havas S (2006) Geneious v2.5, Available from http://www.geneious.com/). The sequences of five aptamers to internalin A are shown in FIG. 7 (SEQ ID NOS: 21-25).

4. ELISA Screening of Aptamers

Figure 6:
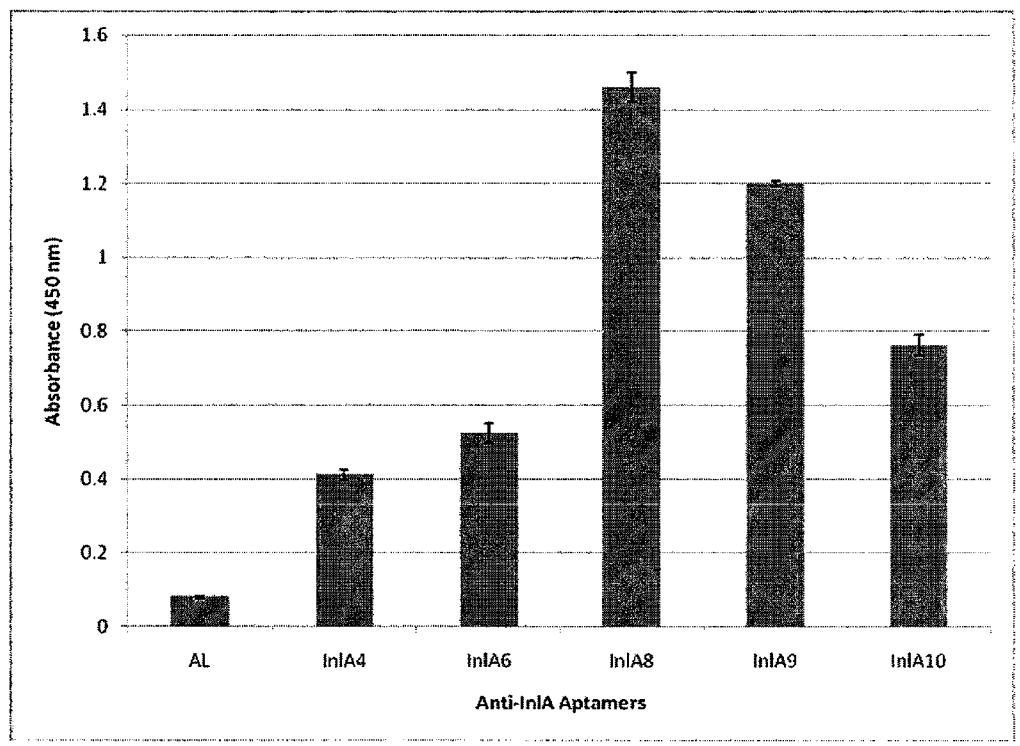
FIG. 6 is a chart showing the results of an ELISA used to screen for selected oligonucleotides that bound to histidine-tagged internalin A attached to a microplate. The initial aptamer library was used as a negative control. The data represents the average±S.D. of n=3.
Figure 9:
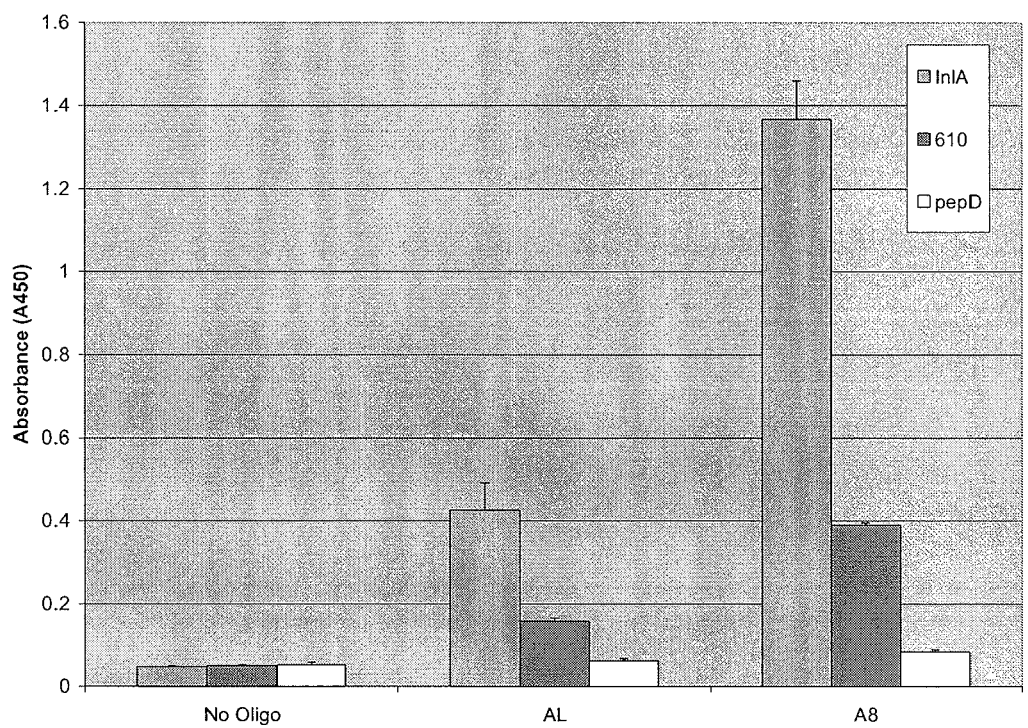
FIG. 9 shows ELISA data for no oligo, aptamer library (AL), internalin A8 aptamer (A8, SEQ ID NO:21) binding to histidine-tagged inlA protein, 0610 protein and peptide D (amino acid sequence obtained from p60 protein: QQQTAP-KAPTEHHHHHH (SEQ ID NO:17)). The amount of selected aptamer bound to the particular proteins was determined by absorbance measured. The data represents the average±S.D. of n=3. The A8 aptamer shows some specificity based on higher signals obtained when incubated with inlA compared to the 0610 protein and peptide D.

A nickel-coated microplate (HisSorb, Qiagen) was used to bind 500 ng his-tagged inlA, peptide D or 0610 (*Listeria monocytogenes*-specific non-internalin cell wall protein) to the plate as per manufacturer's directions. Biotinylated aptamer or aptamer library (5 ng/μL) was heated to 95° C. for 3 minutes and quickly cooled to 4° C. for 5 minutes before application to each well. The biotinylated aptamer or aptamer library was incubated with the bound proteins in the HisSorb plate overnight at 4° C. with gentle shaking. Wells were then washed four times with 200 μL PBS-T. Streptavidin-horseradish peroxidase was added to the wells for 30 minutes at room temperature with gentle shaking. The wells were washed as described previously before development with TMB (Pierce). The reactions were stopped with 1M $H_2SO_4$ and absorbance was measured at 450 nm using a ThermoMax microplate reader (Molecular Devices). The results are shown in FIG. 6. In FIG. 6, the initial aptamer library was used as a negative control, and the data represents the average±S.D. of n=3. Furthermore, FIG. 9 shows further ELISA data for no oligo, aptamer library (AL), and internalin A8 aptamer (A8, SEQ ID NO:21) binding to histidine-tagged inlA protein, 0610 protein and peptide D (amino acid sequence obtained from p60 protein: QQQTAPKAPTEHHHHHH (SEQ ID NO:17)). The amount of selected aptamer bound to the particular proteins was determined by absorbance measured. The data represents the average±S.D. of n=3. The A8 aptamer shows some specificity based on higher signals obtained when incubated with inlA compared to the 0610 protein and peptide D.

5. Competitive ELISA

Figure 10:
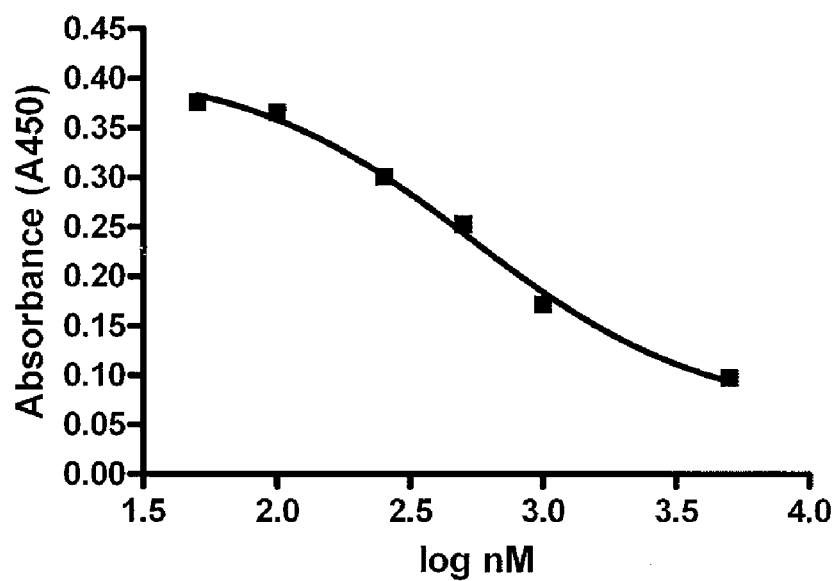
FIG. 10 is data obtained using a competitive ELISA for internalin A8 aptamer (SEQ ID NO:21). The data was input into a sigmoidal model equation, a+(b−a)/(1+10^(x−c)), to obtain an EC50=543.5 nM.

The competitive ELISA was used to measure EC50 (50% effective concentration). A specified amount of internalin A (500 ng) was coated on the plate. 5 ng/uL biotinylated aptamer A8 (SEQ ID NO:21) was incubated with increasing amounts of non-biotinylated aptamer A8 and then applied to the coated plates. Using GraphPad Prism 4 software, the Sigmoidal model (equation: $a+(b-a)/(1+10^{\wedge}(x-c))$) was used to determine EC50. The best-fit value of EC50 was determined to be 543.5 nM. The results are shown in FIG. 10.

6. Whole Cell ELISA

Figure 8:
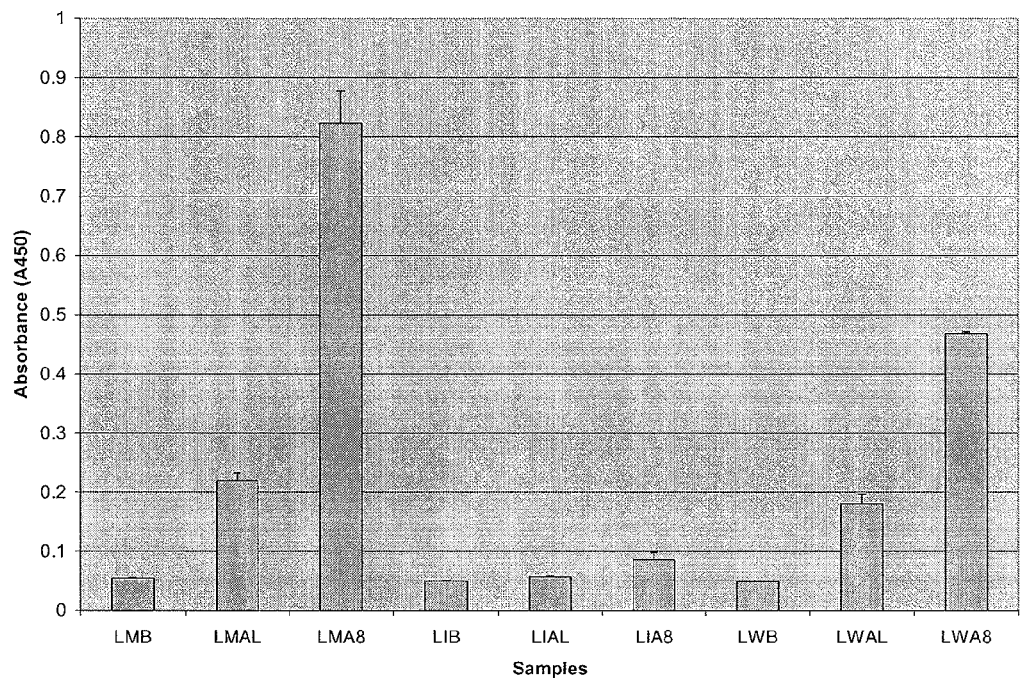
FIG. 8 is a chart showing the results of an ELISA used to test the binding of a selected aptamer designated A8 (having the DNA sequence of SEQ ID NO:21) to whole cells. Approximately $10^7$ cfu of Listeria monocytogenes (LM), Listeria innocua (LI) and Listeria welshimeri (LW) were resuspended in carbonate buffer and allowed to adsorb in the wells. No aptamer (B) or a concentration of 2.5 ng/µL A8 aptamer or aptamer library (AL) was applied to the appropriate wells. Binding was detected using TMB and HRP. The data represent the average±S.D. of n=3. The A8 aptamer demonstrates preferential binding to LM compared to LI and LW.

*Listeria monocytogenes* (LM), *Listeria innocua* (LI) and *Listeria welshimeri* (LW) were grown overnight in Brain Heart Infusion (BHI) broth at 37° C. Approximately $10^7$ cfu were resuspended in carbonate buffer and adsorbed to Immulon 1B flat bottom polystyrene microtiter strips (Thermo Labsystems, #6301) overnight at 4° C. After washing four times in PBS-T, 2.5 ng/μL biotinylated aptamer library (AL), a selected aptamer designated A8 (having the DNA sequence of SEQ ID NO:21), or no aptamer (B) was applied to the wells. Bound library or aptamer was detected using streptavidin-HRP and TMB substrate. The reactions were stopped with 1M $H_2SO_4$ and absorbance was measured at 450 nm using a ThermoMax microplate reader (Molecular Devices). The results are shown in FIG. 8. In FIG. 8, the data represent the average±S.D. of n=3. The A8 aptamer demonstrates preferential binding to LM compared to LI and LW.

7. BIAcore Surface Plasmon Resonance

The affinity of the A8 aptamer for internalin A was measured using surface plasmon resonance (SPR) with a BIAcore 3000 instrument (BIAcore, Piscataway, N.J.). Biotinylated aptamer was heated to 95° C. and rapidly cooled at 4° C. before use. Approximately 100 RU of biotinylated aptamer was immobilized to one flow cell of a streptavidin coated sensor chip. Purified internalin A was diluted into PBS-T to give a series of concentrations of internalin A protein (7.8, 15.6, 31.25, 62.5, 125, 250, 400 nM) that were injected over the surface for 2 min at a flow rate of 30 μL/min. Non-specific interactions with the streptavidin were subtracted using the response from a reference flow cell. After measuring the off rates for 2 min, complete regeneration of the surface was achieved with 0.06% SDS. The affinity, as described by the equilibrium dissociation constant ($K_D$), was determined globally by fitting to the kinetic simultaneous $k_d/k_a$ model, assuming Langmuir (1:1) binding. The $K_D$ of the A8 aptamer for internalin A was $8.35 \times 10^{-8}$ M with $k_a$ (1/Ms) $4.53 \times 10^4$ and $k_d$ (1/s) $3.78 \times 10^{-3}$.

Use of Aptamers in Biosensor Applications

Aptamers such as those described above possess highly advantageous qualities for use in biosensor applications. Aptamer synthesis is potentially far cheaper and more reproducible than antibody-based diagnostic tests. Aptamers may be produced by solid phase chemical synthesis, an accurate and reproducible process with consistency among production batches. Aptamers can be produced in large quantities by polymerase chain reaction (PCR) and aptamers having known sequences, such as those disclosed herein, can be assembled from individual naturally occurring nucleotides and/or synthetic nucleotides. Aptamers are stable to long-term storage at room temperature, and, if denatured, aptamers can easily be renatured, a feature not shared by antibodies. Furthermore, aptamers have the potential to measure concentrations of ligand in orders of magnitude lower (parts per trillion or even quadrillion) than antibody-based diagnostic tests. These inherent characteristics of aptamers make them attractive for diagnostic applications such as biosensors.

A number of "molecular beacons" (often fluorescence compounds) can be attached to the disclosed aptamers to provide a means for signaling the presence of and quantifying a target chemical or biological agent. For instance, an aptamer specific for cocaine has recently been synthesized (Stojanovic; M. N. et al., "Aptamer-based folding fluorescent sensor for cocaine," J. Am. Chem. Soc., 123(21):4928:31 (2001)). A fluorescence beacon, which quenches when cocaine is reversibly bound to the aptamer is used with a photodetector to quantify the concentration of cocaine present. Aptamer-based biosensors can be used repeatedly, in contrast to antibody-based tests that can be used only once.

Of particular interest as a beacon are amplifying fluorescent polymers (AFP). AFPs with a high specificity to TNT and DNT have been developed. It has been noted that a detector based on AFP technology, with high specificity to TNT and DNT, can also detect propofol, an intravenous anesthetic agent, in extremely low concentrations. The combination of AFP and aptamer technologies holds the promise of robust, reusable biosensors that can detect compounds in minute concentrations with high specificity.

The present disclosure relates to methods for diagnosing the presence of Listeria in a sample by detecting the presence of the inlB and inlA proteins in the sample. In accordance with the present disclosure, nanostructure-based assemblies are created in accordance with the method disclosed in, for example, Melker, et al., U.S. Pat. No. 7,052,854, in which the detecting mechanism is designed to specifically detect and localize the assembly to inlB or inlA proteins or both. Nanoparticles in the form of a nanotube that is hollow and has a first open end and a second closed end are employed. A surrogate marker (preferably a volatile compound such as DMSO) is enclosed within the hollow interior of the nanotube. The first open end is blocked with an aptamer-end-cap that prevents the release of the surrogate marker located within the hollow interior of the nanotube. Upon detecting a target analyte/biomarker by the aptamer attached to an end-cap, the surrogate marker is released with the uncapping of the nanoparticle. The uncapping mechanism may require the use of energy-bearing biomolecular motors such as, but not limited to, the actin-based system (Dickinson, R. B. and D. L. Purich, "Clamped filament elongation model for actin-based motors," Biophys. J., 82:605 617 (2002)). Once the nanoparticle is uncapped, the released surrogate marker can then be detected using sensor technology known in the art including, but not limited to, gas chromatography, electronic noses, spectrophotometers to detect the surrogate marker's infrared (IF), ultraviolet (UV), or visible absorbance or fluorescence, or mass spectrometers.

In a preferred embodiment, the detecting mechanism is an aptamer designed to bind to the inlB or inlA proteins or both. A sample from, e.g, a food source or a patient's bodily fluid is placed into a sealed vial containing the nanostructure-based assemblies described in Melker '854.

In one embodiment, the sample is incubated at an elevated temperature to allow any surrogate markers that were released from the nanostructure-based assemblies to diffuse out of the liquid phase into the "headspace" (gas phase) within the sealed vial. Under constant conditions of temperature, pressure, and equilibration time, the vapor phase in the sample vial is sampled and separated on a suitable gas chromatographic column. The surrogate markers are detected using flame ionization detector or nitrogen phosphorous detector.

In another embodiment, an "electronic nose" is used to detect and measure the amount of surrogate marker released in the sample via to assess whether *Listeria* is present in the food or bodily samples. The electronic nose can include the following components: (a) a sensor having an array of polymers capable of detecting the presence of the surrogate marker in the headspace of the vial, wherein the sensor responds to the surrogate marker by changing the resistance in each polymer resulting in a pattern change in the sensor array; (b) a processor for receiving the change in resistance, comparing the change in resistance with a previously measured change in resistance, and identifying the presence of the surrogate marker from the pattern change, and (if requested) the concentration of the surrogate marker from the amplitude. In a related embodiment, the sensor can include measuring circuitry and an output device can be included (i.e., screen display, audible output, printer). The processor can include a neural network for comparing the change in resistance with a previously measured change in resistance to find a best match.

By measuring levels of inlB or inlA or both using the nanostructure-based assemblies of this disclosure, a clinician can not only identify if a sample is currently contaminated with *Listeria*, but in the case of a clinical diagnosis of listeriosis, a clinician can follow the course of the infection. Moreover, by continuously testing samples of bodily fluid in accordance with the present disclosure, it is possible to evaluate the efficacy of interventions in real-time for treating listeriosis. Accordingly, the method of the present disclosure can also evaluate pharmacodynamics and pharmacokinetics for drug interventions in individuals.

Other techniques which may be employed in producing biosensors using the aptamers disclosed herein include those disclosed in, for example, U.S. Pat. Nos. 7,029,852; 6,974,706; 6,897,073; 6,890,719; and 6,399,302, which are incorporated herein by reference.

Biosensor technology may also be used in conjunction with techniques incorporating immunomagnetic capture of bacteria. In this procedure, antibodies to the bacteria of interest are immobilized on magnetic beads. The beads, with attached antibodies or aptamers, interact with the target organisms, which can be separated from other sample material and microorganisms in a magnetic field. This procedure is intended to reduce or eliminate the 24-48 hour enrichment period conventionally required to concentrate the target bacteria in the test sample. Production and use of magnetic beads have been described in U.S. Pat. Nos. 3,970,518; 4,230,685; 4,677,055; 4,695,393 and 5,695,946, which are incorporated herein by reference. Immunomagnetic beads have been used to isolate *Salmonella* (Vermunt et al., J. Appl. Bact. 72, 112, 1992), *Staphylococcus aureus* (Johne et al., J. Clin. Microbiol. 27, 1631, 1989) and *Listeria* (Skjerve et al., Appl. Env. Microbiol. 56, 3478, 1990) from foods, and *Escherichia coli* from fecal samples (Lund et al., J. Clin. Microbiol. 29, 2259, 1991). Immunomagnetic beads can be used to capture bacteria prior to application onto a biosensor platform for improved sensitivity.

Use of Aptamers in Listeriosis Therapy or Prevention

Disclosed aptamers that specifically bind the active site of the inlB or inlA proteins that are involved in promoting *Listeria* infection would be expected to have the effect of inhibiting the development of listeriosis.

Therapeutic compositions of the aptamers may be administered parenterally by injection, although other effective administration forms, such as intraarticular injection, inhalant mists, orally active formulations, transdermal iontophoresis or suppositories, are also envisioned. One preferred carrier is physiological saline solution, but it is contemplated that other pharmaceutically acceptable carriers may also be used. In one preferred embodiment, it is envisioned that the carrier and the ligand constitute a physiologically-compatible, slow release formulation. The primary solvent in such a carrier may be either aqueous or non-aqueous in nature. In addition, the carrier may contain other pharmacologically-acceptable excipients for modifying or maintaining the pH, osmolarity, viscosity, clarity, color, sterility, stability, rate of dissolution, or odor of the formulation. Similarly, the carrier may contain still other pharmacologically-acceptable excipients for modifying or maintaining the stability, rate of dissolution, release, or absorption of the ligand. Such excipients are those substances usually and customarily employed to formulate dosages for parental administration in either unit dose or multidose form.

Once the therapeutic composition has been formulated, it may be stored in sterile vials as a solution, suspension, gel, emulsion, solid, or dehydrated or lyophilized powder. Such formulations may be stored either in a ready to use form or requiring reconstitution immediately prior to administration. The manner of administering formulations containing nucleic acid ligands for systemic delivery may be via subcutaneous, intramuscular, intravenous, intranasal or vaginal or rectal suppository.

In some cases, nucleic acid sequences such as these aptamers are themselves susceptible to enzymatic degradation. This may be counteracted by administering the aptamers in a protected form.

One way in which this may be done is to bind the aptamers to a protective molecule in order to prevent degradation, as disclosed for example in U.S. Pat. No. 7,005,132. For example, an aptamer that specifically binds and inhibits inlB or inlA is protected against enzymatic degradation by administration in specifically bound form. The specific binding partner of the anti-inlB or anti-inlA aptamer may be either a synthetic receptor selected from a combinatorial shape library or an oligonucleotide that hybridizes to the aptamer through Watson-Crick base pairing with a suitable degree of complementarity to yield quasi-stable hybrids that are dissociable in the presence of inlB or inlA. These oligonucleotides are generated by in vitro evolution from initial sequence segments complementary to different nucleotide sequences of the anti-inlB or anti-inlA aptamer. In this embodiment, at least one inlB or inlA aptamer is selected for specific binding to a relatively conserved region of inlB or inlA from a randomized pool or combinatorial shape library comprising oligonucleotides generated by in vitro evolution. Potentially useful shape libraries include, without limitation, populations of polymeric conformers prepared from random combinations of amino acids, nucleotides, carbohydrates and other organic monomers. Selected synthetic receptors are first evaluated in vitro for effectiveness in protecting aptamers against enzymatic degradation through stability studies of corresponding prodrug complexes and control (unbound) aptamers. Synthetic receptors affording protection are then tested for their ability to efficiently deliver aptamers to therapeutic targets in vitro. Prodrug complexes comprising each selected aptamer specifically bound to each selected synthetic receptor are incubated alone and in combination with isolated preparations of inlB or inlA, and the rate, degree and duration of inhibition of infection are compared with control conditions (inlB or inlA alone, inlB or inlA plus aptamer(s), inlB or inlA plus synthetic receptor(s)). Selected prodrug complexes and combinations are then tested for safety and efficacy in preclinical and clinical studies.

Example 1

A patient having clinical indications of listeriosis is intravenously administered a dose of one of the aptamers shown in FIG. 1 or FIG. 7 in a dose of 5 mg/kg per day for 15 days. This may be administered in a single dose, or may be administered as a number of smaller doses over a 24-hour period: for example, three smaller doses at eight-hour intervals. Following treatment, a significant proportion of the inlB or inlA protein is bound by the aptamer and the listeriosis infection is ameliorated.

Example 2

A patient at risk for developing listeriosis (for example as a result of consuming food known to be contaminated with *Listeria monocytogenes*) is intravenously administered a dose of one of the aptamers shown in FIG. 1 or FIG. 7 in a dose of 5 mg/kg per day for 15 days. This may be administered in a single dose, or may be administered as a number of smaller doses over a 24-hour period: for example, three smaller doses at eight-hour intervals. Following treatment, a significant proportion of the inlB or inlA protein is bound by the aptamer.

What is claimed is:

1. An isolated aptamer comprising a nucleic acid molecule that comprises SEQ ID NO: 21.

2. A method of assaying a sample for the presence of *Listeria monocytogenes*, comprising:
   exposing the sample to an aptamer according to claim 1; and
   determining that *Listeria monocytogenes* is present in the sample when the aptamer binds the protein present in the sample.

3. A method of assaying a sample comprising a protein selected from the group consisting of *Listeria monocytogenes* internalin B protein and *Listeria monocytogenes* internalin A protein for the presence of *Listeria monocytogenes*, comprising:

exposing the sample to the aptamer of claim 1; and determining that *Listeria monocytogenes* is present in the sample when the aptamer binds the protein present in the sample.

4. An in vitro diagnostic test kit comprising the aptamer of claim 1 and reagents for detecting aptamer bound to *Listeria monocytogenes* internalin A or B protein.

5. A biosensor comprising the aptamer of claim 1.

6. The biosensor of claim 5, wherein the aptamer is coated on magnetic beads.

7. The biosensor of claim 5, further comprising a nanostructure-based assembly.

8. The biosensor of claim 7, wherein the nanostructure-based assembly comprises:

nanoparticles in the form of a hollow nanotube comprising a first open end and a second closed end; and a surrogate marker enclosed within the hollow interior of the nanotube, wherein the first open end is initially blocked with an end-cap comprising aptamer molecules that prevents the release of the surrogate marker and wherein removing the end-cap releases the surrogate marker.

9. A method of determining the amount of *Listeria monocytogenes* present in a sample using the biosensor of claim 8, comprising:

removing the end-cap to release the surrogate marker; and determining the amount of surrogate marker released.

10. A method of concentrating *Listeria monocytogenes* bacteria in a sample, comprising:

passing the sample over magnetic beads coated with the aptamer of claim 1; and separating the beads from the material in the sample.

11. Magnetic beads coated with the aptamer of claim 1.

* * * * *

UNITED STATES PATENT AND TRADEMARK OFFICE
CERTIFICATE OF CORRECTION

PATENT NO. : 7,838,242 B2
APPLICATION NO. : 12/374480
DATED : November 23, 2010
INVENTOR(S) : Cindy Yamamoto and Toshit Sen It is certified that error appears in the above-identified patent and that said Letters Patent is hereby corrected as shown below:

On page 1, Item 57, Abstract, line 3, delete "InIB" and insert --InlB--, therefor.
On page 1, Item 57, Abstract, line 5, delete "InIB" and insert --InlB--, therefor.
On page 1, Item 57, Abstract, line 8, delete "InIA" and insert --InlA--, therefor.
On page 1, Item 57, Abstract, line 10, delete "InIA" and insert --InlA--, therefor.
At column 2, line 50, delete "(2004))" and insert --(2004)).--, therefor.
At column 7, line 6, delete "InIB" and insert --InlB--, therefor.
At column 7, line 8, delete ""InIB-" and insert --"InlB- --, therefor.
At column 7, line 10, delete "InIB" and insert --InlB--, therefor.
At column 7, line 13, delete ""InIB," and insert --"InlB,--, therefor.
At column 9, line 38, delete "InIB-" and insert --InlB- --, therefor.

Signed and Sealed this
Eighteenth Day of October, 2011

David J. Kappos
*Director of the United States Patent and Trademark Office*

SEQUENCE LISTING

```
<160> NUMBER OF SEQ ID NOS: 25

<210> SEQ ID NO 1
<211> LENGTH: 16
<212> TYPE: DNA
<213> ORGANISM: Artificial Sequence
<220> FEATURE:
```

-continued

```
<223> OTHER INFORMATION: Consensus sequence for aptamers to internalin B

<400> SEQUENCE: 1
gggyygggrg ggyggg                                               16

<210> SEQ ID NO 2
<211> LENGTH: 16
<212> TYPE: DNA
<213> ORGANISM: Artificial Sequence
<220> FEATURE:
<223> OTHER INFORMATION: Consensus sequence for aptamers to internalin B

<400> SEQUENCE: 2
gggytgggag ggyggg                                               16

<210> SEQ ID NO 3
<211> LENGTH: 15
<212> TYPE: DNA
<213> ORGANISM: Artificial Sequence
<220> FEATURE:
<223> OTHER INFORMATION: Consensus sequence for aptamers to internalin B
<223> OTHER INFORMATION: n=a or g or c or t

<400> SEQUENCE: 3 gggngghgg grggg                                                 15

<210> SEQ ID NO 4
<211> LENGTH: 15
<212> TYPE: DNA
<213> ORGANISM: Artificial Sequence
<220> FEATURE:
<223> OTHER INFORMATION: Consensus sequence for aptamers to internalin B

<400> SEQUENCE: 4
gggdggghgg grggg                                                15

<210> SEQ ID NO 5
<211> LENGTH: 16
<212> TYPE: DNA
<213> ORGANISM: Artificial Sequence
<220> FEATURE:
<223> OTHER INFORMATION: Consensus sequence for aptamers to internalin B

<400> SEQUENCE: 5
gggrgggrrg ggyggg                                               16

<210> SEQ ID NO 6
<211> LENGTH: 30
<212> TYPE: DNA
<213> ORGANISM: Artificial Sequence
<220> FEATURE:
<223> OTHER INFORMATION: Internalin B PCR primer

<400> SEQUENCE: 6
ggtattgagg gtcgcgcgaa agtacaagcg                                30

<210> SEQ ID NO 7
<211> LENGTH: 34
<212> TYPE: DNA
<213> ORGANISM: Artificial Sequence
<220> FEATURE:
<223> OTHER INFORMATION: Internalin B PCR primer

<400> SEQUENCE: 7
agaggagagt tagagccttt ctgtgcccTT aaat                           34
```

```
<210> SEQ ID NO 8
<211> LENGTH: 78
<212> TYPE: DNA
<213> ORGANISM: Artificial Sequence
<220> FEATURE:
<223> OTHER INFORMATION: Aptamer library
<223> OTHER INFORMATION: n=a or g or c or t

<400> SEQUENCE: 8
ggtattgagg gtcgcatcnn nnnnnnnnnn nnnnnnnnnn nnnnnnnnnn nnnnnnnnga      60
tggctctaac tctcctct                                                   78

<210> SEQ ID NO 9
<211> LENGTH: 18
<212> TYPE: DNA
<213> ORGANISM: Artificial Sequence
<220> FEATURE:
<223> OTHER INFORMATION: LIC-F PCR primer

<400> SEQUENCE: 9
ggtattgagg gtcgcatc                                                   18

<210> SEQ ID NO 10
<211> LENGTH: 20
<212> TYPE: DNA
<213> ORGANISM: Artificial Sequence
<220> FEATURE:
<223> OTHER INFORMATION: LIC-R PCR primer

<400> SEQUENCE: 10
agaggagagt tagagccatc                                                 20

<210> SEQ ID NO 11
<211> LENGTH: 18
<212> TYPE: DNA
<213> ORGANISM: Artificial Sequence
<220> FEATURE:
<223> OTHER INFORMATION: Aptamer to internalin B

<400> SEQUENCE: 11
cgggagggcg gggggggct                                                  18

<210> SEQ ID NO 12
<211> LENGTH: 41
<212> TYPE: DNA
<213> ORGANISM: Artificial Sequence
<220> FEATURE:
<223> OTHER INFORMATION: Aptamer to internalin B

<400> SEQUENCE: 12
cacgggaggg aagggtgggc aagtggagac acaaactttc a                         41

<210> SEQ ID NO 13
<211> LENGTH: 41
<212> TYPE: DNA
<213> ORGANISM: Artificial Sequence
<220> FEATURE:
<223> OTHER INFORMATION: Aptamer to internalin B

<400> SEQUENCE: 13
ctgggctggg agggtgggct atatatctgt acattttcg a                          41

<210> SEQ ID NO 14
<211> LENGTH: 42
<212> TYPE: DNA
```

```
<213> ORGANISM: Artificial Sequence
<220> FEATURE:
<223> OTHER INFORMATION: Aptamer to internalin B

<400> SEQUENCE: 14
ttgggtggga gggagggttg agaacaagaa tccgcaaatg tt                    42

<210> SEQ ID NO 15
<211> LENGTH: 41
<212> TYPE: DNA
<213> ORGANISM: Artificial Sequence
<220> FEATURE:
<223> OTHER INFORMATION: Aptamer to internalin B

<400> SEQUENCE: 15 attgggggggg tgggagggac gcagcgcaat ttcccaacgg t                    41

<210> SEQ ID NO 16
<211> LENGTH: 41
<212> TYPE: DNA
<213> ORGANISM: Artificial Sequence
<220> FEATURE:
<223> OTHER INFORMATION: Aptamer to internalin B

<400> SEQUENCE: 16
caaatgggtt gggagggcgg gcaataaagc acttacgttg g                     41

<210> SEQ ID NO 17
<211> LENGTH: 17
<212> TYPE: PRT
<213> ORGANISM: Artificial Sequence
<220> FEATURE:
<223> OTHER INFORMATION: Peptide D obtained from p60 protein

<400> SEQUENCE: 17

Gln Gln Gln Thr Ala Pro Lys Ala Pro Thr Glu His His His His His
  1               5                  10                  15

His

<210> SEQ ID NO 18
<211> LENGTH: 17
<212> TYPE: DNA
<213> ORGANISM: Artificial Sequence
<220> FEATURE:
<223> OTHER INFORMATION: Consensus sequence for internalin A aptamers

<400> SEQUENCE: 18
gggyaggggr gggwggg                                                17

<210> SEQ ID NO 19
<211> LENGTH: 33
<212> TYPE: DNA
<213> ORGANISM: Artificial Sequence
<220> FEATURE:
<223> OTHER INFORMATION: Internalin A PCR primer

<400> SEQUENCE: 19
ggtattgagg gtcgcacaaa tgctcaggca gct                              33

<210> SEQ ID NO 20
<211> LENGTH: 38
<212> TYPE: DNA
<213> ORGANISM: Artificial Sequence
<220> FEATURE:
<223> OTHER INFORMATION: Internalin A PCR primer
```

-continued

```
<400> SEQUENCE: 20
agaggagagt tagagcctta tgaagcttct tttgaatt                                    38

<210> SEQ ID NO 21
<211> LENGTH: 47
<212> TYPE: DNA
<213> ORGANISM: Artificial Sequence
<220> FEATURE:
<223> OTHER INFORMATION: Aptamer to Internalin A

<400> SEQUENCE: 21
atccatgggg cggagatgag ggggaggagg gcgggtaccc ggttgat                          47

<210> SEQ ID NO 22
<211> LENGTH: 47
<212> TYPE: DNA
<213> ORGANISM: Artificial Sequence
<220> FEATURE:
<223> OTHER INFORMATION: Aptamer to Internalin A

<400> SEQUENCE: 22
atctaggact gggtgggaag ggatgggaaa aatgtccgcg cctcgat                          47

<210> SEQ ID NO 23
<211> LENGTH: 47
<212> TYPE: DNA
<213> ORGANISM: Artificial Sequence
<220> FEATURE:
<223> OTHER INFORMATION: Aptamer to Internalin A

<400> SEQUENCE: 23
atcagcaaca agtgtgggta aggggagggc gggaatggga tgatgat                          47

<210> SEQ ID NO 24
<211> LENGTH: 47
<212> TYPE: DNA
<213> ORGANISM: Artificial Sequence
<220> FEATURE:
<223> OTHER INFORMATION: Aptamer to Internalin A

<400> SEQUENCE: 24
atcggatgtg ggcagggggg ggtgggaaac gattacagac acaagat                          47

<210> SEQ ID NO 25
<211> LENGTH: 47
<212> TYPE: DNA
<213> ORGANISM: Artificial Sequence
<220> FEATURE:
<223> OTHER INFORMATION: Aptamer to Internalin A

<400> SEQUENCE: 25
atcgggttat agttagcggg taggggaggg agggtagata gctcgat                          47
```